United States Patent [19]

Byers et al.

[11] Patent Number: 4,952,506

[45] Date of Patent: Aug. 28, 1990

[54] IMMOBILIZATION OF NONANCHORAGE-DEPENDENT CELLS

[75] Inventors: Michael J. Byers, Gwynedd; Eric G. Isacoff, Richboro; John O. Naples, Dresher, all of Pa.

[73] Assignee: Rohm and Haas Company, Philadelphia, Pa.

[21] Appl. No.: 854,982

[22] Filed: Apr. 28, 1986

[51] Int. Cl.$^5$ .......................... C12N 5/02; C12N 1/00
[52] U.S. Cl. .............................. 435/240.25; 435/243; 435/180; 435/240.26; 435/942
[58] Field of Search ...................... 435/240.22, 240.25, 435/240.26, 261, 182, 240.24, 942, 948, 181, 177, 180, 243, 255

[56] References Cited

U.S. PATENT DOCUMENTS

Re. 29,130  2/1977  Lee et al. ............................ 435/261
4,036,693  10/1977  Levine et al. .................. 435/240.24
4,347,320  8/1982  Borglum ............................ 435/182
4,380,590  4/1983  Chong .................................... 521/29

Primary Examiner—Charles F. Warren
Assistant Examiner—Gail E. Poulos

[57] ABSTRACT

Nonanchorage-dependent cells are immobilized for cell culturing or the production of cell products, by contracting an aqueous suspension of the cells with a floc formed by the combination of positively and negatively charged ion exchange resins having particle sizes ranging from about 0.01 to about 1.5 microns. The flocs may be formed either prior to contract with the cells or may be formed in situ in the cell suspension upon separate addition of the resins, preferably by first adding the positively charged resin followed by the negatively charged resin. The resin floc operates as a microcarrier for the cells.

7 Claims, No Drawings

IMMOBILIZATION OF NONANCHORAGE-DEPENDENT CELLS

Technical Field

This invention relates to cell culturing and the production of products therefrom, and more particularly to the immobilization of nonanchorage-dependent cells with microcarriers.

Background of the Invention

U.S. Pat. Nos. 4,266,032 to Miller et al, 4,189,534 and 4,293,654, both to Levine et al, PCT patent application WO Ser. No. 82/00660, published 4 Mar. 1982 and European Patent Application No. 66726, published 15 Dec. 1982 review and disclose culturing methods based on the use of microcarrier supports for attachment of growing cells.

In the Miller et al patent, the microcarrier comprises a cross-linked polystyrene resin derivatized with an amino acid, a peptide or a hydroxy carboxylic acid. A resin bead size range of 20–64 microns diameter and usefulness in growing anchorage dependent cells is described. The Levine et al patents disclose positively charged ion exchange resins having a particle size of approximately 75 microns in the dry state or an average diameter of about 120–200 microns in the case of hydrated beads. Both patents are directed to use of the resins as microcarriers for growing anchorage-dependent cells. The patents mention that the microcarriers can also be used for the growth of other type cells, but no examples or description of other cell types is given.

The microcarriers of the PCT patent application are naturally occurring proteins or polysaccharides such as gelatin or chitosan, which may be cross-linked. The microcarriers of the European Patent Application comprise anion exchange resins wherein the functional groups are quarternary amine groups which resist degradation. The resins of both applications are used for culturing of anchorage-dependent cells only.

Anchorage-dependent and nonanchorage-dependent cells differ markedly in their culturing requirements. Anchorage-dependent cells require attachment to a solid substrate for viability. Many commercially valuable products, including proteins, carbohydrates, lipids, or complexes of these materials or others, are produced by cells grown while attached to such microcarriers, the attachment resulting from functional groups on the polymeric particles and a microcarrier density slightly greater than the surrounding culture medium. The microcarriers permit a cell concentration far greater than can be achieved in monolayer culture, and enhance the ease with which the cell products can be recovered and purified. Consequently, the yield of desired product is greatly increased.

Many biologically important substances, such as monoclonal antibodies obtained from hybridoma cells, are produced in nonanchorage-dependent cells or in cells that attach to surfaces with low efficiency. (In this specification, "nonanchorage-dependent" is intended to mean and include both of the last-mentioned types of cells). Non-anchorage-dependent cells will grow in suspension, but culturing conditions that maintain a high cell number per volume of medium, and therefore a high mass productivity for the products, require high rates of medium exchange for supply of adequate nutrients. The required high rate of medium exchange, particularly when achieved by conventional perfusion culture, may result in the washing out of the suspended cells and therefore substantial loss of product.

This difficulty has been mitigated to some extent by providing some type of physical barrier, such as a membrane, ceramic or centrifugal filter, between the cells and the effluent medium. However, such specialized equipment, or modifications to existing equipment, add considerably to the complexity and cost of culturing nonanchorage-dependent cells and the production of useful products therefrom.

Summary of the Invention

It has now been found that nonanchorage-dependent cells may be immobilized such that they may be cultured in suspension and maintained in perfusion culture with substantially reduced cell loss and without need for additional specialized filters or other equipment. These benefits are achieved by contacting an aqueous suspension of the nonanchorage-dependent cells with a floc formed by combining positively charged and negatively charged ion exchange resin particles. The resin floc binds and supports the cells to form a complex which can be easily removed from the suspension by filtering or other means.

To achieve good contact between the resin floc and the cells, the suspension containing the cells and floc preferably is agitated. Generally, upon cessation of the agitation, the floc carrying the cells settles rapidly to the bottom of the vessel. This permits change of the culturing medium without cell loss. Optionally, because the effective size of the cell mass has been greatly increased, physical barriers such as filters may be used to facilitate removal of the cell-floc complex.

In one aspect of the invention, therefore, a method of immobilizing nonanchorage-dependent cells, for the more efficient culturing of cells or the production of products therefrom, is provided by contacting a nonanchorage-dependent, cell-containing culturing medium with a floc formed by combining positively charged and negatively charged, particulate ion exchange resins. The cells bind to the resins and are supported thereon, thus facilitating cell growth.

Other aspects of the invention include a microcarrier system for cell culturing or the production of products therefrom, comprising a floc carrying nonanchorage-dependent cells thereon, wherein the floc is formed by contacting a cell-containing culturing medium with a resin floc formed by combining positively charged and a negatively charged, particulate ion exchange resins, and a cell culturing method wherein nonanchorage-dependent cells are supported on the resin floc for more efficient growth and production of useful products from the cells.

The foregoing and other aspects, features and benefits of the invention will become more apparent from the description which follows.

Detailed Description

In one embodiment of the invention, the cell immobilization method is practiced by adding a positively or negatively charged ion exchange resin to a culturing medium containing nonanchorage-dependent cells, agitating the mixture to disperse the ion exchange resin throughout the medium, and then contacting the resultant mixture with an ion exchange resin carrying a charge opposite the charge of the first-added resin. Preferably, the first resin is positively charged and the later-added resin is negatively charged. A floc will immediately begin to form as a result of aggregation between the oppositely charged resins. The floc will bind the cells and the floc carrying the cells will precipitate when quiescent conditions are attained. If desired, contact with the second-added resin and the resultant flocculation can be accelerated and controlled by agitation of the mixture as in the first step.

The amounts of resins to be added to the cell suspensions will depend on the cell concentration, charge densities of both the cells and the resins, particle size and porosity of the resins, and other factors appreciated by those skilled in the art, such as the pH of the suspension, the isoelectric points of other materials or cell products in the medium, and affinities of the cells, materials or products to the resins. Generally, the resins may be employed on an equal weight basis with the cells, but considerable variation is possible depending on the factors mentioned.

If it is desired to transfer or store the immobilized cells, the flocculated material carrying the cells thereon may be separated from the medium by filtration or other convenient means. The immobilized cells may then be resuspended for culturing and/or production of enzymes, antibiotics or other substances characteristic of the cell system.

Alternatively, cell culturing may be practiced by maintaining the flocculated material in the medium rather than separating it, and perfusing as needed. This is conveniently achieved because the cells, when immobilized on the resin floc, rapidly settle to the bottom of the vessel, thus permitting change of medium without cell loss. Optionally, physical supports, conventional for the culturing of nonanchorage-dependent cells, may be employed to even greater advantage than heretofore, because of the increased effective size of the cell mass afforded by the immobilization.

While not fully understood, it is believed that the immobilization results from the initial interaction of the positively charged resin with the negatively charged cell surface, the subsequently added negatively charged resin then acting as a bridging agent to form clumps of cell/resin complexes as the oppositely charged resins flocculate.

In another embodiment of the invention, the resin floc may be preformed prior to contact with the cell culture. This is conveniently achieved by admixing the oppositely charged resins in aqueous suspension and then adding the suspension to the cell culturing medium, with agitation as needed. Cell immobilization is thereby effected and the resulting cell mass carried in the floc may be separated or perfused as already described.

Any particulate ion exchange resins having sufficient charge densities (ion exchange capacities) and proportions for effective electrostatic attraction to the cells and interaction to form flocs, may be employed, provided, however, that the resins have particle sizes in the range of about 0.01 to about 5 microns, preferably about 0.01 to about 1.5 microns and more preferably about 0.1 to about 1 micron, on an average diameter basis. The small particle size means that the resins have large surface area/volume ratios, thereby combining good adsorbent properties with electrostatic attraction. Useful positively charged resins include any of the resins described in the aforementioned U.S. patents which are water insoluble and produced with the requisite particle size or whose particle size is subsequently reduced by grinding.

Generally, both the positively charged and negatively charged resins are prepared by first forming a cross-linked copolymer matrix, usually by suspension polymerization but also by emulsion polymerization, and then functionalizing the copolymer particles to provide the requisite charge and charge density. A wide variety of monomers, both for forming the backbone and crosslinks, are useful, including the various well-known vinyl aromatic and acrylic monomers, as described in standard texts on the subject, including *Ion Exchange*, J. Marinsky, Ed., Volume II, Chapter 6 (New York, 1969).

Preferred ion exchange resins are described in U.S. Pat. Nos. 4,200,695 to Chong, Isacoff and Neely; 4,359,537 and 4,380,590 to Chong; and 4,537,683 to Isacoff and Neely. The resins of these patents are, generally speaking, ion exchange resins composed of cross-linked polymers in the shape of approximately spherical beads, produced by emulsion polymerization. Useful resins bear 0.1–1.5 functional groups per monomer unit, defining charge density, but other functional group ratios may be used. The positively charged resins can be strongly acidic (e.g., —$SO_3H$ groups) or weakly acidic (e.g., —COOH groups) and the negatively charged resins may be either strongly basic (e.g., quarternary ammonium groups) or weakly basic (e.g., tertiary amine groups).

The resin disclosures of all of the foregoing patents, patent applications and publications are incorporated herein by reference.

Of course, the resins should be non-toxic and should be rendered sterile in the usual manner for use in the invention.

The culture medium is any liquid system known in the art for the culturing of nonanchorage-dependent cells, the specific composition depending, of course, on the types of cells to be immobilized and/or cultured in accordance with the invention. Usually, the liquid culturing medium will contain nutrients which supply sources of carbon and nitrogen as well as various salts, buffering agents and other ingredients needed for pH control and for maximum growth and production.

The invention is applicable to any nonanchorage-dependent cells (animal, plant, microbial or genetically engineered) and will result in clusters of higher cell numbers than normally are obtainable in suspension culturing. Typically, cells which can be aggregated in accordance with the invention include lymphocytes, other blood cells, cells of tumor origin, cells formed by fusions, transformed cell lines such as CHO and HeLa, and laboratory modified strains of these cells. Generally, the cells may have any animal or plant origin and which the art has shown to be capable of suspension or attached culturing. The invention is also applicable to single cell organisms, such as yeast, algae and bacteria.

As separated immobilized cells, the cells can be used in bioreactors as a source of biologically or chemically active products. Such bioreactors may comprise agitated, submerged, deep tank types, as well as airlift or insoluble matrix reactors, and the bioreactors may be used in either batch or perfusion modes.

Other conditions for optimizing the practice of the invention will be apparent to those skilled in the art, including concentrations of ion exchange resins, pH and temperature control, choice of nutrients and other ingredients for cell growth, means and conditions for agitating cultures, and methods for recovering cell products, and reference is made to the voluminous literature on such subjects.

The following examples are intended as further illustration of the invention but not necessarily to limit the scope thereof. In the examples, all parts and percentages are by weight unless otherwise specified.

Example 1

To 50 million CHO cells in a total of 25 milliliters of Ham's F12 culture medium were added 50 microliters of sterile 1% wt/wt suspension of a quarternary amine functionalized, emulsion polymerized styrene-divinylbenzene gellular copolymer resin, 1.8% crosslinker, having an average particle diameter of 0.22 ± 0.02 micron and an anion exchange capacity of 3.8 meq/g dry (Resin A). The mixture was thoroughly stirred and to the dispersion was added 100 microliters of sterile 1% wt/wt suspension of a sulfonic acid functionalized, emulsion polymerized styrene-divinylbenzene gellular copolymer resin, 7.3% cross-linker, having an average particle diameter of 0.26 ± 0.02 micron and a cation exchange capacity of 5.1 meq/g dry (Resin B).

The resultant floc settled to the bottom of the vessel, was separated and then resuspended in 25 milliliters of Ham's F12 culture medium. The floc was maintained in this medium at 37° C. in a 5% $CO_2$-95% air atmosphere for 7 days with medium changes as necessary. Microscopic observation indicated that initial flocs were open-structured with distinct cells being visible, thus demonstrating cell immobilization. Single cells were observed after seven days outside of the cell/resin clumps. Upon repetition of the experiment, using 100 microliters of each resin, cell clumps containing a correspondingly larger number of cells were observed.

Example 2

To five million mouse myeloma cells in 50 milliliters of Ham's F12 were sequentially added 1.0 milliliters of sterile 1% wt/wt suspension of Resin A (Example 1) and 0.5 milliliters of sterile 1% wt/wt suspension of Resin B (Example 1). The culture conditions were the same as in Example 1. Microscopic observations over a nine day period indicated that the cells remained viable but no evidence of cell number increase was seen.

Example 3

To five million mouse hybridoma cells in 20 milliliters of Ham's medium was added 1 milliliter of a preformed resin floc prepared by premixing equal mass amounts of Resins A and B (Example 1). The solids content of the preformed floc suspension was 0.5% wt/wt after autoclaving. Most of the cells had attached to the added floc when observed 24 hours later. Production of antibody by the immobilized cells was confirmed by an ELISA assay.

Example 4

1 milliliter of 1% wt/wt suspension of the positively charged resin of Example 1 (Resin A) was added to 10 milliliters of an overnight culture of *Saccaromyces cerevisiae*, followed by 0.5 milliliters of a 1% wt/wt suspension of the negatively charged resin of Example 1 (Resin B). Greater than 95% of the cells settled rapidly to the bottom of the tube. The medium was replaced with 10 milliliters of Sabarouds medium plus 10% glucose every 24 hours. $CO_2$ evolution and ethanol production continued over a five day period.

Example 5

500 million CHO cells were immobilized by treatment with Resins A and B substantially as described in Example 1, differing only in that 500 microliters of 1% wt/wt suspensions of each of the resins was used. The resultant floc was resuspended in 25 milliliters of medium. Cell viability over the seven day observation period was not adversely affected by the increased resin density.

We claim:

1. A cell culturing method which comprises contacting a culturing medium containing living, nonanchorage-dependent cells with a floc formed by the combination of positively and negatively charged ion exchange resins, whereupon the living cells bind to the the floc and are supported thereon, and subsequently culturing the living cells; said resins comprising crosslinked copolymer particles having average diameters in the range of about 0.01 to about 1.5 microns.

2. The method of claim 1 wherein the floc together with the cells carried thereon is permitted to precipitate in the culturing vessel, and the culturing medium above the precipitate is exchanged.

3. The method of claim 1 wherein the resin floc is formed prior to contact with the culturing medium.

4. The method of claim 1 wherein the resin floc is formed in situ upon separate addition of oppositely charged resins to the culturing medium.

5. The method of claim 4 wherein the positively charged resin is dispersed in the culturing medium, followed by addition of the negatively charged resin.

6. The method of claim 1 wherein the resins comprise approximately spherical beads bearing about 0.1 to about 1.5 ion exchange functional groups per monomer unit.

7. The method of claim 1 wherein the cells comprise a CHO cell line, mouse myeloma cells, mouse hybridoma cells, or Saccaromyces cerevisiae cells.

* * * * *